United States Patent [19]

Sogabe et al.

[11] Patent Number: 5,744,342
[45] Date of Patent: Apr. 28, 1998

[54] PROTEIN HAVING HEAT-RESISTANT MALATE DEHYDROGENASE ACTIVITY

[75] Inventors: Atsushi Sogabe; Seiji Takeshima; Kazumi Yamamoto; Shinichi Teshima; Shigenori Emi; Yoshihisa Kawamura, all of Tsuruga, Japan

[73] Assignee: Toyo Boseki Kabushiki Kaisha, Osaka, Japan

[21] Appl. No.: 838,418

[22] Filed: Apr. 7, 1997

Related U.S. Application Data

[63] Continuation of Ser. No. 270,013, Jul. 1, 1994, Pat. No. 5,686,294.

[30] Foreign Application Priority Data

Jul. 2, 1993 [JP] Japan .................................. 5-164701

[51] Int. Cl.$^6$ ...................................................... C12N 9/04
[52] U.S. Cl. ........................................... 435/190; 435/189
[58] Field of Search ........................................ 435/189, 190; 536/23.2

[56] References Cited

PUBLICATIONS

Birkraft et al., "The Presence of a Histidine-Aspartic Acid Pair in the Active Site of 2-Hydroxyacid Dehydrogenases", *J. Biol. Chem.*, 258: 472 (1983).

Iijima et al., "Physicochemical and Catalytic Properties of Thermostable Malate Dehydrogenase From an Extreme Thermophile Thermus Flavus AT-62", *Biochimica et Biophysica Acta*, 613, 1–9 (1980).

Lepock et al., "Thermal Analysis of Bacteria by Differential Scanning Calorimetry: Relationship of Protein Denaturation In Situ to Maximum Growth Temperature", *Biochimica et Biophysica Acta*, 1055, 19–26 (1990).

Murphey et al., "Purification and Properties of *Bacillus subtilis*, *Bacillus stearothermophilus*, and *Escherichia coli* Malate Dehydrogenases", *The Journal of Biological Chemistry*, 242, No. 7, 1548–1559 (1967).

Ohshima et al., "Purification and Characterization of Malate Dehydrogenase from the Phototrophic Bacterium, *Rhodopseudomonas capsulata*", *Biochimica et Biophysica Acta*, 869, 171–177 (1986).

Rolstad et al., "Malate Dehydrogenase from the Thermophilic Green Bacterium *Chloroflexus aurantiacus*: Purification, Molecular Weight, Amino Acid Composition, and Partial Amino Acid Sequence", *Journal of Bacteriology*, 170, No. 7, 2947–2953 (1988).

Sambrook et al., *Molecular Cloning: A Laboratory Manual*, Cold Spring Harbor Laboratory Press, 11.3–11.19 (1989).

Sundaram et al., "Malate Dehydrogenase from Thermophilic and Mesophilic Bacteria, Molecular Size, Subunit Structure, Amino Acid Composition, Immunochemical Homology, and Catalytic Activity", *Biochemistry*, 19, 2017–2022 (1980).

Wilks et al. "A Specific, Highly Active Malate Dehydrogenase by Redesign of a Lactate Dehydrogenase Framework", *Science*, 242, 1541–1544 (1988).

Wright et al. "Simple Efficient Methods for the Isolation of Malate Dehydrogenase from Thermophilic and Mesophilic Bacteria", *Biochem. J.*, 177, 441–448 (1979).

You et al., "Purification and Properties of Malate Dehydrogenase from *Pseudomonas testosteroni*", *Journal of Bacteriology*, 123, No. 2, 704–716 (1975).

*Primary Examiner*—Keith D. Hendricks
*Attorney, Agent, or Firm*—Leydig, Voit & Mayer, Ltd.

[57] ABSTRACT

A novel protein having a heat-resistant malate dehydrogenase activity, a DNA fragment having a gene encoding said protein, a recombinant vector having said DNA fragment, a transformant transformed with said vector, a method for producing the protein having heat-resistant malate dehydrogenase activity by the use of said transformant, a reagent for GOT determination, comprising the above-mentioned novel protein having a heat-resistant malate dehydrogenase activity and a method for determining GOT activity, which comprises the use of said reagent. According to the present invention, a protein having a heat-resistant malate dehydrogenase activity and having higher purity and superior heat stability can be obtained. In addition, a reagent for GOT determination which is superior in long-term storage can be prepared by the use of the protein having a heat-resistant malate dehydrogenase activity.

6 Claims, 3 Drawing Sheets

F I G. 1
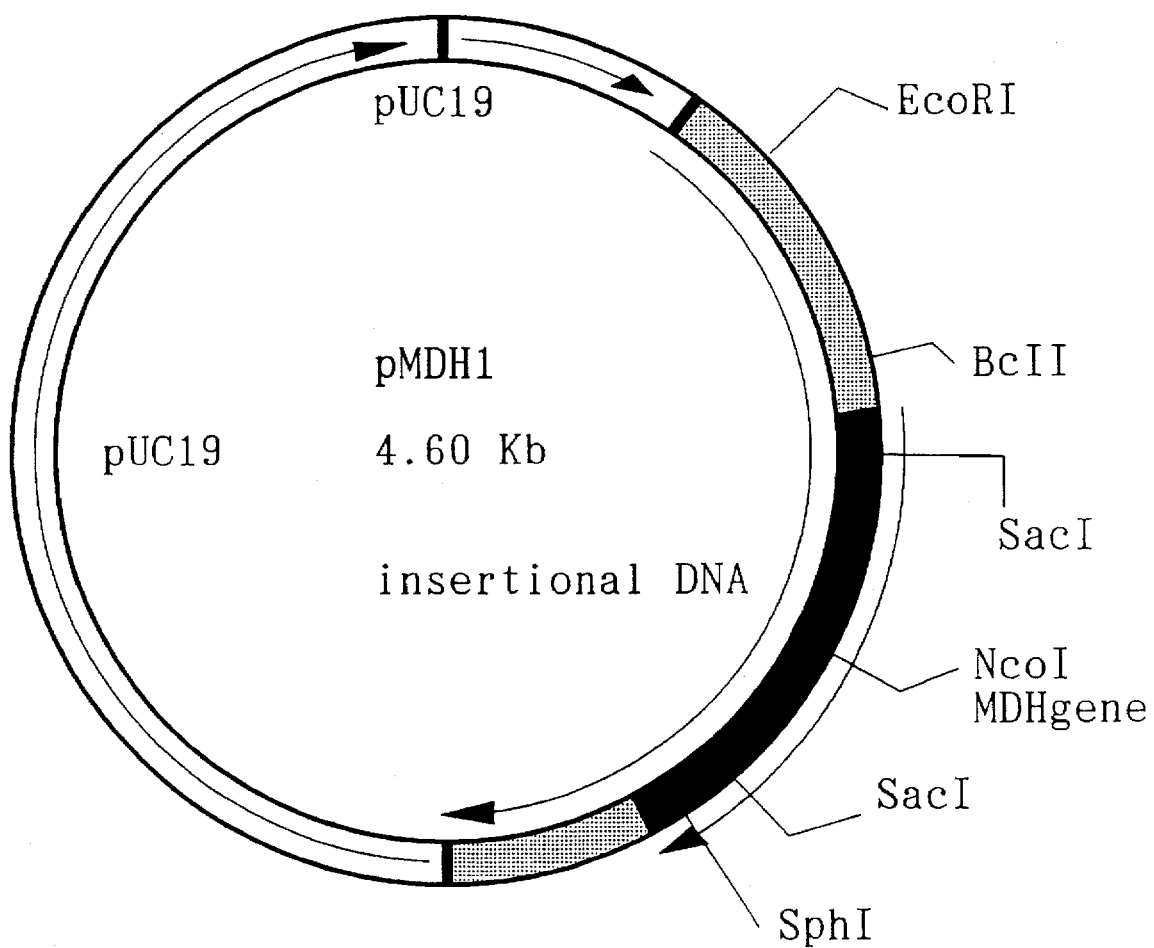

PROTEIN HAVING HEAT-RESISTANT MALATE DEHYDROGENASE ACTIVITY

This is a continuation of application Ser. No. 08/270,013, filed on Jul. 1, 1994, now U.S. Pat. No. 5,686,294.

FIELD OF THE INVENTION

The present invention relates to a novel protein having a heat-resistant malate dehydrogenase activity, which is useful for the determination of glutamic-oxaloacetic transaminase (hereinafter referred to as GOT) activity in blood that is a clinical index for diagnoses of hepatitis and myocardinal infarction and for the measurement of carbon dioxide concentration in plasma that is an index of acid-base imbalance in the respiratory metabolism; a DNA fragment having a gene encoding said protein; a recombinant vector having said DNA fragment; a transformant transformed with said vector; and a method for producing a protein having a heat-resistant malate dehydrogenase activity by using said transformant.

The present invention also relates to a reagent for determining GOT activity, which comprises, as one component, the above-mentioned novel protein having a heat-resistant malate dehydrogenase activity and to a method for determining GOT activity, which comprises the use of said reagent.

BACKGROUND OF THE INVENTION

Malate dehydrogenase (EC 1.1.1.37) is an enzyme which is widely present in animal, plant and microbial sources and is conventionally used in clinical tests, for instance, to determine the GOT activity in blood or carbon dioxide concentration in plasma.

As said enzyme, a malate dehydrogenase derived from the mitochondria of swine heart is generally used. Since the malate dehydrogenase of swine heart is poor in thermalstability, the commercially available reagents for GOT activity measurement comprising said malate dehydrogenase are not satisfactory in that the reagent cannot be stored for a long time in a liquid state.

On the other hand, various malate dehydrogenases derived from bacteria have been found. It is known that mesophilic bacteria such as Corynebacterium, Brevibacterium and Arthrobacter (Japanese Patent Unexamined Publication No. 26396/1979), *Bacillus subtilis* and *Escherichia coli* [J. Biol. Chem., vol. 242, No. 7, 1548–1559 (1967)], *CholorofLexus aurantica* [J. Bacteriol., vol. 170, No. 7, 2947–2953, July (1988)], *Rhodopsuedomonas capsulata* [Biochimica et Biophysica Acta, 869, 171–177 (1986)], and *Pseudomonas testosterni* [J. Bacteriol., vol. 123, No. 2, 704–716, Aug. (1975)] produce malate dehydrogenases which are not heat-resistant. None of them are sufficient in heat stability or have high productivity to realize their practical applications.

It is also known that thermophilic bacteria such as *Thermus thermophilus* (Japanese Patent Unexamined Publication No. 99188/1980), *Thermus Flavus* AT-62 [Biochimica et Biophysica Acta, 613, 1–9 (1980), *Bacillus stearothermophilus* strain UK 788 (Japanese Patent Unexamined Publication No. 148288/1981 corresponding to U.S. Pat. No. 4,331,762) and *Bacillus stearothemtophilus* strain 2184 [J. Biol. Chem., vol. 242, No. 7, 1548–1559 (1967)] produce heat-resistant malate dehydrogenases. The malate dehydrogenase derived from the genus *Thermus sp.* is being sold as a heat stable enzyme. The optimum temperature of this enzyme, however, is as high as around 90° C. and it exhibits low catalytic activity at a temperature near the reaction temperature (generally room temperature) to be employed in clinical tests, thus rendering application of this enzyme to clinical tests unsuitable. The enzyme, moreover, has been found to be not so superior in stability in a reagent for determining GOT activity as is expected from the heat stability that the enzyme has.

The thermal property of the malate dehydrogenase derived from the genus *Bacillus stearothermophilus* strain UK 788 is not certain. As the strain produces other enzymes like heat-resistant acetate kinase together with a malate dehydrogenase, there is a possibility that the purified malate dehydrogenase may be contaminated.

*Bacillus stearothermophilus* strain 2184 also produces heat resistant malate dehydrogenase. But the maximal specific activity assayed at 22° C. for the enzyme of this strain is very low due to its poor activity at this temperature. Therefore, these enzymes derived from *Bacillus stearothermophilus* strains may not have sufficiently high productivity to allow preparation of the reagents for determining GOT activity or may not be superior in stability during long-term preservation.

Accordingly, a malate dehydrogenase superior in reactivity at room temperature and stability during long-term preservation, particularly stability in a reagent for GOT determination, is desired.

SUMMARY OF THE INVENTION

A first object of the present invention is to provide a protein having a heat-resistant malate dehydrogenase activity, which exhibits superior stability in a reagent for determining GOT activity.

A second object of the present invention is to provide a process and materials for supplying said protein in a pure form and in a large amount by genetic engineering.

A third object of the present invention is to provide a reagent for determining GOT activity, which comprises, as one component, the protein of the present invention having a heat-resistant malate dehydrogenase activity.

A fourth object of the present invention is to provide a method for determining GOT activity, which comprises the use of the protein of the present invention having a heat-resistant malate dehydrogenase activity.

With the aim of achieving the aforementioned objects, the present inventors have conducted various studies and found that *Bacillus stearothermophilus* ATCC 12016 has a gene encoding a protein having a heat-resistant malate dehydrogenase activity, and isolated the gene from the chromosomal DNA of the cells thereof, based on which the entire nucleotide sequence has been successfully identified. Further studies resulted in the finding that a transformant into which the gene derived from said *Bacillus stearothermophiLus* ATCC 12016 by genetic engineering has been introduced produces, at high yields, a protein having a heat-resistant malate dehydrogenase activity and exhibiting higher heat resistance and higher specific activity than do the protein produced by the *Bacillus stearothermophilus* ATCC 12016. The studies also resulted in the establishment of a method for producing said protein in a highly purified form at high yields. In the following specification, said protein having a heat-resistant malate dehydrogenase activity of the present invention is also referred to simply as heat-resistant MAD.

BRIEF DESCRIPTION OF THE DRAWINGS

FIG. 1 is a restriction enzyme map of an insertional DNA of pMDH1.

DETAILED DESCRIPTION OF THE INVENTION

Figure 2:
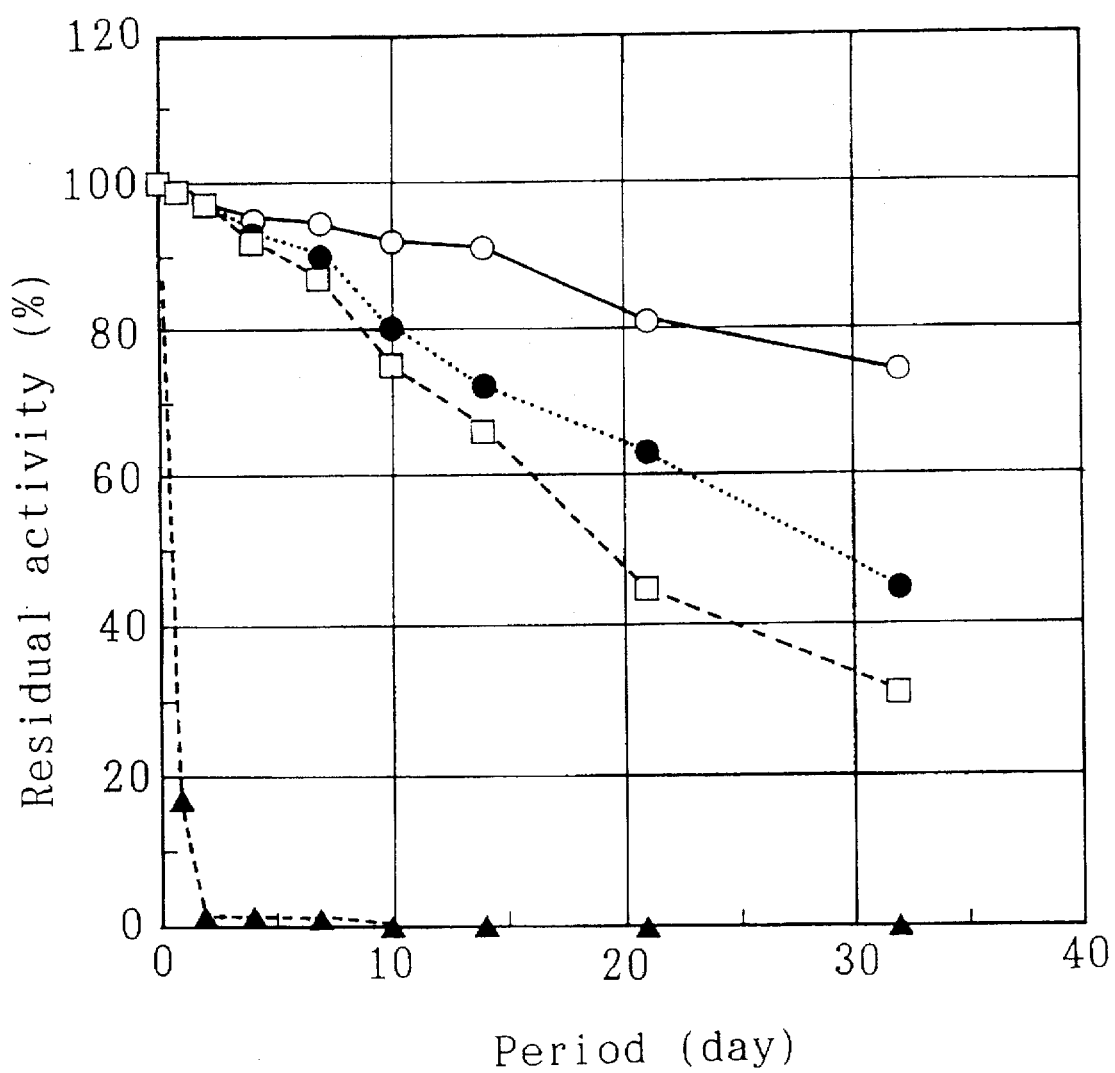
FIG. 2 shows residual malate dehydrogenase activity as determined in Examples 7 and 8, and Comparative Examples 1 and 2.

According to the present invention, there is provided a protein having a heat-resistant malate dehydrogenase activity, which exhibits a residual activity after preservation at 40° C. for 10 days in a solution state of at least 60%.

In addition, the present invention provides a DNA fragment comprising a gene encoding a protein having a heat-resistant malate dehydrogenase activity; a recombinant vector having said DNA fragment; a transformant transformed with said recombinant vector; and a method for producing the protein having a heat-resistant malate dehydrogenase activity, which comprises culturing said transformant in a medium to allow production of the protein having a heat-resistant MAD activity and collecting said protein.

The present invention further provides a reagent for determining GOT activity, comprising NADH, L-aspartic acid, α-ketoglutaric acid, (optionally lactate dehydrogenase) and heat-resistant malate dehydrogenase exhibiting a residual activity after preservation at 40° C. for 10 days in a solution state of at least 60%.

The present invention also provides a method for determining GOT activity, comprising measuring NADH consumed by the GOT measurement reagent comprising NADH, L-aspartic acid, a-ketoglutaric acid, (optionally lactate dehydrogenase) and heat-resistant MAD exhibiting a residual activity after preservation at 40° C. for 10 days in a solution state of at least 60%.

It is essential that the protein having a heat-resistant malate dehydrogenase activity should exhibit a residual activity after preservation at 40° C. for 10 days in a solution state of at least 60%, preferably 70%, more preferably 80% and most preferably 90%.

In the present invention, "a solution state" refers to a solution having the following formulation.

| | |
|---|---|
| Lactate dehydrogenase (optionally used) | 500–2000 U/l |
| Heat-resistant malate dehydrogenase | 500–5000 U/l |
| L-Aspartic acid | 150–250 mmol/l |
| α-Ketoglutaric acid | 10–40 mmol/l |
| NADH | 0.1–0.25 mmol/l |
| Buffer (pH 7.5) | 0.05–0.1 mmol/l |

The residual activity as referred to in the present invention is a ratio (%) of the activity of malate dehydrogenase after preservation of the above-mentioned solution at a given temperature for 10 days, to the MAD activity (100%) before the preservation.

The activity of malate dehydrogenase is measured as in the following.

The following reaction mixture is placed in a cuvette (d=1.0 cm) and pre-heated at 25° C. for about 5 minutes.

| | |
|---|---|
| 0.1 M K-oxaloacetate buffer (pH 7.5) | 2.8 ml |
| 15 mM oxaloacetic acid solution (dissolved in | 0.1 ml |

| | |
|---|---|
| K-phosphate buffer) | |
| 6.0 mM NADH aqueous solution | 0.1 ml |

A solution (0.05 ml) containing the aforementioned heat-resistant MAD is added to the reaction mixture as described above and the mixture is gently mixed. The change in absorbance at 340 nm is measured at 25° C. for 3–4 minutes with a spectrophotometer using water as a control and the change in absorbance per minute is determined from the initial linear portion thereof (ΔOD test). As a blank test, the change in absorbance per minute is determined by doing the same test as above except that 0.05 ml of K-phosphate buffer (pH 7.5) is added in place of the solution containing heat-resistant MAD (ΔOD blank). The MAD 1U (unit) is the amount of the enzyme necessary for oxidizing 1 μmol of NADH per minute under the above-mentioned conditions.

The heat-resistant MAD is not subject to any particular limitation insofar as it has the aforementioned properties and the origin thereof is not limited. Preferably, it is a heat-resistant MAD produced by *Bacillus stearothermophilus* ATCC 12016 strains and more preferably, a heat-resistant MAD produced by a transformant carrying a gene encoding heat-resistant MAD, which is derived from a bacterium belonging to the genus Bacillus, in view of superior heat stability and specific activity to the heat-resistant MAD produced by the ATCC 12016 strains.

The transformant carrying a gene encoding the heat-resistant MAD is not subject to any particular limitation insofar as it is capable of producing the heat-resistant MAD. Preferred are those derived from *Eschelichia coli* or *Bacillus subtilis* and more preferred are those derived from *E. coli* W3110, *E. coli* C600, *E. coli* JM109, *Bacillus subtilis* MI113 or *Bacillus subtilis* MT-2.

The gene encoding the heat-resistant MAD, which is carried by the transformant, may be isolated from a bacterium belonging to the genus Bacillus by a conventional method or may be chemically synthesized. The gene may be of wild type or non-wild type as long as it is capable of encoding the heat-resistant MAD, and is exemplified by a DNA sequence obtained by partial mutation of a wild type DNA sequence of a gene encoding heat-resistant MAD, which is derived from a bacterium belonging to the genus Bacilus.

Preferred gene is a nucleotide sequence having a gene encoding the amino acid sequence depicted in SEQ ID NO:2, more preferably that having a nucleotide sequence depicted in SEQ ID NO:1 to be given later.

The heat-resistant MAD of the present invention preferably has the following properties.

Action: reversibly catalyzes the following reaction.

Substrate specificity: specifically oxidizes L-malic acid or specifically reduces oxaloacetic acid.
Optimum temperature: 70° C.
Optimum pH: 8.0
Heat stability: not more than 70° C.
pH Stability: pH 3.0–9.0
Isoelectric point: 4.8
Molecular weight: 140,000 (gel filtration), 38,000 (SDS-PAGE)
Km value: $4.3 \times 10^{-6}$M (oxaloacetic acid)
Specific activity: 203 U/mg protein The method for obtaining the heat-resistant MAD of the present invention is not limited. For example, a *Bacillus stearothermophilus* ATCC 12016 strain or a transformant carrying a gene encoding heat-resistant MAD may be cultured by a conventional method and the heat-resistant MAD yielded is harvested from the culture, or the heat-resistant MAD may be chemically synthesized by a conventional method.

In the following, an exemplary method for obtaining the heat-resistant MAD of the present invention from a *Bacillus stearothermophilus* ATCC 12016 strain is given.

The medium for culturing said strain may be that containing carbon source, nitrogen source, inorganic ion and where necessary, nitrate, phosphate etc. As the carbon source, usable are sugars from monosaccharides such as glucose and fructose to macromolecular polysaccharides such as dextrin and soluble starch. As the nitrogen source, exemplified are polypepton, trypton, meat extract and yeast extract. Culture is performed until the yield of the malate dehydrogenase reaches maximum at a temperature affording the highest growth of the cells.

The malate dehydrogenase can be isolated from the culture cell and purified as in the following.

Cells are collected by centrifugation of the culture. The cells are disrupted to enable extraction of the malate dehydrogenase. For disrupting, a cell wall lytic enzyme such as lysozyme may be used or physical treatment such as ultrasonication, glass beads disruption or French press disruption may be applied.

The lysate thus obtained is subjected to denucleation by a treatment with polyethyleneimine and a malate dehydrogenase fraction is recovered by ammonium sulfate fractionation. The malate dehydrogenase fraction thus obtained is desalted by G-25 gel filtration and purified to a higher degree by DEAE Sepharose CL-6B column chromatography (Pharmacia LKB, Sweden)→Phenyl Sepharose CL-6B column chromatography (Pharmacia LKB, Sweden)→TSK gel G-3000 SW gel (Toyo Soda, Japan) filtrations and MonoP HR5/5 chromatofocusing (Pharmacia LKB, Sweden). The purified product migrates as a single band on SDS polyacrylamide gel electrophoresis (SDS-PAGE). While the combination of the column chromatographys is not limited to that mentioned above, several steps of column chromatographies may be necessary for achieving a single band on electrophoresis.

The DNA fragment of the present invention is subject to no particular limitation insofar as it has a nucleotide sequence encoding the heat-resistant MAD as described earlier. For example, a DNA fragment comprising a nucleotide sequence encoding the amino acid sequence as listed in SEQ ID NO:2 or a DNA fragment comprising a nucleotide sequence as listed in SEQ ID NO:1 may be used. In addition, a DNA fragment having a nucleotide sequence as listed in SEQ ID NO:1, which underwent partial mutation such as deletion, substitution, addition or modification, may be used.

The DNA fragment of the present invention may be isolated from a bacterium belonging to the genus Bacillus, preferably *Bacillus stearothermophilus* and more preferably *Bacillus stearothermophilus* ATCC 12016 strain by a conventional method, or may be chemically synthesized by a conventional method.

For example, the DNA fragment of the present invention is prepared as in the following. First, a chromosomal DNA of a bacterium belonging to the genus Bacillus, preferably *Bacillus stearothermophilus* ATCC 12016 is isolated and purified. Said DNA is cleaved by ultrasonication or with restriction enzyme and the DNA fragment obtained is ligated with a lineared expression vector at the blunt ends or cohesive ends of the both DNAs by the use of a DNA ligase etc. to give a recombinant vector. The recombinant vector thus obtained is introduced into a replicatable host to construct a gene library. From this gene library, a microorganism (donor microorganism) carrying a recombinant vector having a heat-resistant MAD-encoding DNA is obtained by screening with the use of a marker of the vector and heat-resistant MAD activity as indices. Then, the obtained donor microorganism is cultured under aeration for about 1 to 3 days in a liquid medium and the culture obtained is centrifuged to collect cells. The cells are lysed to give a lysate containing the heat-resistant MAD gene. For lysis, a lytic enzyme such as lysozyme or β-glucanase may be used along with, where necessary, protease, other enzyme or a surfactant such as sodium lauryl sulfate, or a physical treatment such as freeze-thawing or ultrasonication may be used together with the above-mentioned lytic treatment on demand.

DNA is isolated and purified by appropriately combining conventional methods such as deproteinization by extraction with phenol, protease treatment, treatment with ribonuclease and alcohol precipitation.

The obtained DNA is prepared into a DNA fragment of the present invention by ultrasonic treatment, treatment with restriction enzyme and the like, preferably by the treatment with a II-type restriction enzyme.

The recombinant vector of the present invention has the aforementioned DNA fragment of the present invention and is preferably capable of autonomic proliferation in *E. coli* or *Bacillus subtitis*.

The recombinant vector of the present invention is preferably an expression vector inducing the host cell (e.g. *E. coli*, *Bacillus subtilis*) to express the gene encoding the heat-resistant MAD for the production of the heat-resistant MAD.

Said recombinant vector is prepared by integrating the DNA fragment of the present invention into a vector for expression with ease.

Preferable vector for expression is that for use in genetic recombination, which is constructed from a phage or a plasmid capable of autonomic proliferation in a host microorganism.

Examples of the phage when, for example, *E. coli* is used as a host microorganism include λ gt 10 and λ 11.

Examples of the plasmid when, for example, *E. coli* is used as a host microorganism include pBR322 and pUC19. When *Bacillus subtilis* is used as a host microorganism, pUB110, pC19 or the like may be used. In addition, a shuttle vector (e.g. pHY300PLK) capable of autonomic proliferation in two or more Gram negative or Gram positive host microorganisms such as *E. coli* and *Bacillus subtilis* may be used.

So as to give a lineared vector fragment, it is preferable that such vector for expression should be cleaved with the same restriction enzyme as that used for the cleavage of the donor microorganism mentioned earlier. The DNA fragment of the present invention is ligated with said vector fragment by a conventional method using DNA ligase. For example, a cohesive end or a blunt end of the DNA fragment of the present invention is annealed with that of the vector fragment and ligated with them by the use of a suitable DNA ligase to construct a recombinant vector having the DNA fragment of the present invention. Where necessary, the annealed DNA fragment-vector fragment is introduced into a host microorganism to allow biological DNA ligase to construct a recombinant vector therefrom.

The transformant of the present invention is transformed with the aforementioned recombinant vector of the present invention and can be prepared by introducing said recombinant vector into a host microorganism by a conventional method.

The host microorganism may be any insofar as the recombinant vector of the present invention can be present stably therein, is capable of autonomic proliferation therein and extraneous gene is capable of transformation therein, and examples thereof include *E. coli* W3110, *E. coli* C600, *E. coli* JM109, *Bacillus subtilis* MI113 and *Bacillus subtilis* MT-2.

A recombinant vector may be transformed into a host microorganism by, for example, recombinant DNA incorporation in the presence of a calcium ion when the host microorganism belongs to the genus *E. coli*, and by a competent cell method [J. Mol. Biol., 56, 209 (1971)], a protoplast method [Mol. Gen. Genet. 168, 111 (1979)] or electropolation [Cell, vol. 48, 813–825 (1987)] when the host microorganism belongs to the genus Bacillus. The transformant microorganism thus obtained has been found to stably produce a large amount of the protein having heat-resistant malate dehydrogenase activity when it is cultured in a nutrient medium. The selection of the host microorganism with respect to the transformation of the object recombinant vector may be based on a search for a host microorganism capable of concurrently expressing both a drug resistant marker and the heat-resistant MAD of the vector carrying the object DNA. For example, a microorganism capable of growing in a medium containing the drug, the medium being selected according to the drug resistant marker, as well as producing heat-resistant MAD may be selected.

So as to distinguish over the heat-labile malate dehydrogenase derived from the host microorganism, the heat-resistant MAD of the present invention is detected as follows. That is, cultured cells are disrupted and treated with heat at 65° C. for 30 minutes to completely inactivate the malate dehydrogenase derived from the host microorganism, whereafter the malate dehydrogenase activity caused by the heat-resistant MAD of the present invention is determined.

The recombinant vector of the present invention carrying the heat-resistant MAD gene is taken out from the transformant microorganism and can easily transform other microorganism. It can also be easily done to cleave out the heat-resistant MAD gene from the recombinant vector of the present invention carrying the heat-resistant MAD gene by the use of a restriction enzyme etc., ligating same with a vector fragment obtained by cleaving in the same manner as above and transforming the host microorganism.

According to the method of the present invention, a heat-resistant MAD is produced by culturing the aforementioned transformant of the present invention. The culture is done under the conditions selected in view of the nutritive-biological properties of the host and liquid culture is generally selected, though from an industrial viewpoint, aerobic spinner culture is advantageous. The carbon source of the medium may be any that is widely used for culture of transformants, insofar as the host microorganism can utilize same, such as glucose, sucrose, lactose, maltose, fructose, honey and pyruvic acid. The nitrogen source may be any that is utilizable by the host microorganism, such as organic nitrogen compound (e.g. pepton, meat extract, yeast extract, hydrolysate of casein, soybean lees extracted with alkali) and inorganic nitrogen compounds such as ammonium sulfate and ammonium chloride. Besides these, usable as necessary are salts such as phosphate, carbonate, sulfate, magnesium, calcium, potassium, iron, manganese and zinc, particular amino acids and particular vitamins.

The temperature of culture may be appropriately varied within the range wherein the host microorganism grows and produces the heat-resistant MAD. In the case of *E. coli*, it is preferably about 20°–42° C. While the culture period somewhat varies depending on culture conditions, the culture may be terminated when the yield of the heat-resistant MAD has reached maximum, which is about 20–48 hours. The pH of the medium may be varied within the range wherein the host microorganism grows and produces the heat-resistant MAD, which is preferably about pH 6.0–9.0.

The cells are recovered from a liquid culture by a conventional method such as centrifugation and filtration. When the heat-resistant MAD in the liquid culture is secreted outside the cells, the cell-removed culture can be used, from which the heat-resistant MAD is isolated and purified by the following method subsequent to cell lysis.

When the heat-resistant MAD is present intracellularly, it can be extracted upon lysis by enzymatic or physical treatment as mentioned above. The thus-obtained solution containing the heat-resistant MAD is treated with heat at a temperature permitting inactivation of the malate dehydrogenase derived from the host but not permitting inactivation of the target heat-resistant MAD (for example, the treatment at 65° C. for 30 minutes) to remove the malate dehydrogenase derived from the host. Then, the nucleic acid is removed by a treatment with a hydrophilic polymer such as polyethyleneimine and the heat-resistant MAD fraction is recovered by precipitation with ammonium sulfate.

The recovered heat-resistant MAD solution is subjected to a heat treatment for a long time under the conditions which do not cause inactivation of the target heat-resistant MAD, for example, a treatment at 60° C. for 16 hours to denature the contaminant protein derived from the host to allow removal thereof as an insoluble protein. The insoluble protein is removed by a conventional method such as centrifugation or filtration.

The heat-resistant MAD solution is subjected to desalting by a conventional method, such as dialysis using a semipermeable membrane or gel filtration on Sephadex G-25 (Pharmacia LKB, Sweden).

The heat-resistant MAD solution is then adjusted to pH 4.0 with an acid solution such as acetic acid solution and separated and purified by column chromatography such as ion exchange chromatography, preferably CM-Sepharose CL-6B (Pharmacia LKB, Sweden) to give a purified heat-resistant MAD product. This product migrates as a single band on SDS-PAGE.

The heat-resistant MAD to be obtained by the method of the present invention has a residual activity after preservation at 40° C. for 10 days in a solution state of at least 60%, preferably 70%, more preferably 80% and most preferably 90%, and preferably has the following properties.

Action: reversibly catalyzes the following reaction.

Substrate specificity: Specifically oxidizes L-malic acid or specifically reduces oxaloacetic acid.
Optimum temperature: 70° C.
Optimum pH: 8.0
Heat stability: not more than 70° C.
pH Stability: pH 3.0–9.0
Isoelectric point: 4.8
Molecular weight: 140,000 (gel filtration), 38,000 (SDS-PAGE)

Km value: 4.3×10$^{-6}$M (oxaloacetic acid)
Specific activity: 203 U/mg protein

This heat-resistant MAD differs from the heat-resistant MAD produced by *Bacillus stearothermophilus* ATCC 12016 in terms of heat stability and specific activity. That is, the heat-resistant MAD produced by *Bacillus stearothermophitus* ATCC 12016 exhibits heat stability of not more than 65° C. and specific activity of 103 U/mg protein, whereas the heat-resistant MAD produced by the transformant having the maleate dehydrogenase activity exhibits heat stability of not more than 70° C. and specific activity of 203 U/mg protein.

The reagent for GOT determination of the present invention is characterized by the aforementioned heat-resistant MAD of the present invention and is superior in long-term storability. Besides the heat-resistant MAD, the reagent contains NADH, α-ketoglutaric acid and L-aspartic acid, and optionally lactate dehydrogenase.

While the lactose dehydrogenase is not directly involved with the GOT reaction, it is useful for determining the oxaloacetic acid produced in the first reaction in the GOT determination. That is, the presence of lactose dehydrogenase prevents change of oxaloacetic acid to pyruvic acid by decarboxylation, which in turn aids precise determination of NAD$^+$ conversion velocity, i.e. GOT amount (Japanese Patent Unexamined Publication Nos. 39799/1982, 53298/1982, 175898/1984).

The lactate dehydrogenase to be used in the present invention may be of any origin insofar as the residual activity after preservation at 40° C. for 10 days in a solution state is at least 60%. For example, those derived from animal organs such as bovine heart or swine heart and those derived from lactic acid bacteria are usable, with preference given to those derived from lactic acid bacteria which are superior in stability.

The reagent for GOT determination of the present invention may be a one component or two component solution. Example of the two component reagent is a mixture of a first reagent containing a heat-resistant MAD of the present invention, lactate dehydrogenase, NADH and a-ketoglutaric acid or L-aspartic acid and a second reagent containing L-aspartic acid or α-ketoglutaric acid.

An exemplary composition of the reagent of the present invention is shown below. The figures express concentration or enzyme activity obtained after mixing the first reagent and the second reagent.

| | |
|---|---|
| Lactate dehydrogenase (optional) | 500–2000 U/l |
| Heat-resistant MAD of the invention | 500–5000 U/l |
| L-Aspartic acid | 150–250 mmol/l |
| α-Ketoglutaric acid | 10–40 mmol/l |
| NADH | 0.1–0.25 mmol/l |
| Buffer | 0.05–0.1 mmol/l |

As the buffer, desirable are Tris-HCl, sodium phosphate, potassium phosphate and GOOD buffer. The reagent of the present invention preferably has a pH of 7.0–8.0.

The method of the present invention for determining GOT activity is characterized by the use of the aforementioned reagent for GOT determination. The method comprises bringing a GOT determination test sample into contact with a reagent of the present invention and determining, based on the decrease in absorbance at 340 nm, the conversion speed of NADH in the reagent into NAD$^+$ through the reactions of

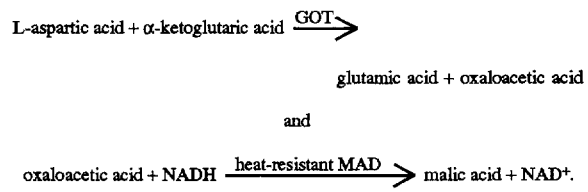

In general, GOT activity unit per 1 l of a sample is calculated as follows.

$$\text{GOT activity (U/l)} = \frac{(\Delta A/\text{min}) \times \text{dilution of sample}}{\mu\text{mol molecular absorbance coefficient of NADH}}$$

The GOT IU (international unit) is defined as an enzyme amount necessary for consuming 1 μmol of NADH per minute at 30° C.

The protein of the present invention is a novel, heat-resistant MAD having a residual activity after preservation at 40° C. for 10 days in a solution state of at least 60%. According to the present invention, the nucleotide sequence of the heat-resistant malate dehydrogenase has been clarified and industrial mass production thereof has become attainable.

The production method of the present invention, moreover, has enabled production of a heat-resistant MAD having higher purity than and superior heat stability to the heat-resistant MAD produced by a wild type strain ATCC 12016.

According to the present invention, a reagent for GOT determination which is superior in long-term storage, can be prepared by the use of the heat-resistant MAD having a residual activity upon preservation at 40° C. for 10 days in a solution state of at least 60%. The reagent of the present invention is extremely advantageous in view of the fact that liquid reagents are increasingly used in many fields, since it is stable in a liquid state.

The present invention is hereinafter explained in detail by way of Examples.

In the Examples, activity of the heat-resistant MAD was determined as in the following.

The heat-resistant MAD was reacted in 97 mM potassium phosphate buffer (pH 7.5), 0.49 mM oxaloacetic acid and 0.2 mM NADH at 25° C. for 3–4 minutes and absorbance at 340 nm was determined. One unit of the enzyme activity is an enzyme amount necessary for oxidizing 1 μmol NADH per minute under these conditions.

EXAMPLE 1

Purification of Heat-Resistant MAD from *Bacillus stearothermophilus* ATCC 12016

*Bacillus stearothermophilus* ATCC 12016 was cultured in a jar fermenter. The culture was performed in an LB medium (1% polypepton, 0.5% yeast extract and 0.5% NaCl, pH 7.4) containing 1% sodium acetate at 50° C. for 26 hours with aeration. The yield was about 1.2 U/ml. The culture obtained (5.2 l) was centrifuged to separate about 30 g of cells. The cells were suspended in 50 mM potassium phosphate buffer, pH 7.5, and lysed by the treatment with lysozyme to give about 2 l of cell lysate. The heat-resistant malate dehydrogenase activity at this time was about 3.1 U/ml. The lysate was subjected to denucleation by the treatment with polyethyleneimine, after which heat-resistant MAD fraction was recovered by precipitation with ammonium sulfate and resuspended in 50 mM potassium phosphate buffer (pH 7.5). The specific activity at this time was 0.16 U/mg protein.

The suspension of ammonium sulfate precipitation was desalted with Sephadex G-25 (Pharmacia LKB, Sweden). The desalted solution was subjected to DEAE Sepharose CL-6B (Pharmacia LKB, Sweden) column chromatography bufferized with 50 mM potassium phosphate buffer, pH 7.5, and eluted with a gradient of between 0.15M and 0.35M NaCl. Then, the resultant solution was subjected to Phenyl Sepharose CL-6B (Pharmacia LKB) column chromatography bufferized with 50 mM potassium phosphate buffer (pH 7.5) containing ammonium sulfate having 0.15 saturation degree, washed with ammonium sulfate having 0.15–0.0 saturation degree and eluted with 0–50% ethylene glycol. Then, the enzyme solution was subjected to gel filtration through TSKgelG-3000SW (manufactured by Tokuyama Soda, Japan) bufferized with 50 mM potassium phosphate buffer (pH 7.5) containing 0.2M NaCl. Thereafter, the enzyme solution was subjected to MonoP HR5/5 chromatofocusing (Pharmacia LKB) and eluted with a gradient of between pH 6.0 and pH 4.5. The heat-resistant MAD product obtained by the present method showed a single band on SDS-PAGE and had specific activity of 108.0 U/mg protein.

The above-mentioned purifications are summarized in Table 1. The physicochemical properties of the heat-resistant MAD obtained by the method above are shown in Table 2.

TABLE 1

Purification of heat-resistant MAD from
*Bacillus stearothermophilus* ATCC 12016

| step | total activity (U) | specific activity (U/mg-protein) | yield (%) |
|---|---|---|---|
| lysozyme-treated solution | 6200 | — | 100 |
| polyethyleneimine-treated solution | 5890 | 0.08 | 95 |
| resuspension of ammonium sulfate precipitation | 3250 | 0.16 | 52 |
| G-25-desalted solution | 3280 | 0.21 | 53 |
| DEAE Sepharose | 3470 | 0.76 | 56 |
| Phenyl Sepharose | 2770 | 12.0 | 45 |
| TSK G-3000SW | 2200 | 74.4 | 35 |
| MonoP HR5/5 | 1540 | 108.0 | 25 |

TABLE 2

Physicochemical properties of heat-resistant MAD purified
from *Bacillus stearothermophilus* ATCC 12016

| item | |
|---|---|
| Action | L-Malate + NAD$^+$ ←→ Oxaloacetate + NADH + H$^+$ |
| Substrate specificity | specific oxidation of L-malic acid or specific reduction of oxaloacetic acid |
| Optimum temperature | 65° C. |
| Optimum pH | pH 8.0 |
| Heat stability | not more than 65° C. |
| pH stability | pH 3.0–9.0 |
| Isoelectric point | 4.8 |
| Molecular weight | 140,000 (gel filtration) 38,000 (SDS-PAGE) |
| Km value | $4.0 \times 10^{-6}$ M (oxaloacetic acid) |
| Specific activity | 108 U/mg-protein |

EXAMPLE 2

Isolation of Chromosomal DNA

The chromosomal DNA of *Bacillus stearothermophilus* ATCC 12016 was isolated by the following method.

The cell was subjected to shake culture in 150 ml of bouillon medium at 60° C. overnight and the culture was centrifuged (8000 rpm, 10 min) to collect cells. The cells were suspended in a solution (5 ml) containing 10% sucrose, 50 mM Tris-HCl (pH 8.0) and 50 mM EDTA and 1 ml of lysozyme solution (10 mg/ml) was added thereto. The mixture was incubated at 37° C. for 15 minutes and 1 ml of 10% SDS solution was added thereto. An equivalent amount of chloroform-phenol solution (1:1) was added thereto ad the mixture was stirred. The mixture was subjected to centrifugation at 10,000 rpm for 3 minutes to separate a water layer from a solvent layer and the water layer was partitioned. A 2-fold amount of ethanol was gently layered on the water layer and DNA was isolated by winding same around a glass rod which was gently whirled therein.

The DNA was dissolved in 10 mM Tris-HCl buffer, pH 8.0, containing 1 mM EDTA (hereinafter abbreviated as TE), which was then treated with an equivalent amount of chloroform-phenol solution. Centrifugation of the resultant solution separated a water layer and a two-fold amount of ethanol was added thereto. In the same manner as above, DNA was again isolated and dissolved in 2 ml of TE.

The competent cell of *Eschelichia coli* JM109 was prepared by the method of Hanahan [Proc. Natl. Acad. Sci., USA, 75, 1927 (1978)] and used as a host for the construction of a library.

EXAMPLE 3

Preparation of DNA Fragment Comprising a Gene Encoding Heat-Resistant MAD and Recombinant Vector Comprising Said DNA Fragment DNA (1 µg) as obtained in Example 2 was partially disintegrated with restriction enzyme Sau3AI (manufactured by Toyo Boseki Kabushiki Kaisha, Japan) into fragements of not less than 2 kbp. The DNA fragment was ligated with pUC19 (0.5 µg) cleaved with SalI (manufactured by Toyo Boseki Kabushiki Kaisha, Japan) by a reaction with 1 unit of T4DNA ligase (manufactured by Toyo Boseki Kabushiki Kaisha, Japan) at 16° C. for 12 hours according to the backfilling method of M. G. Loftus et al. [Biotechniques Vol. 12, No. 2 (1992)]. The ligated DNA was transformed with competent cell of *Eschelichia coli* JM109. The colonies of the transformant were obtained at about $1 \times 10^6$ per 1 µg of the DNA used.

The obtained colonies were cultured in an LB medium (5 ml, 1% polypepton, 0.5% yeast extract, 0.5% sodium chloride) containing 50 µg/ml ampicillin at 37° C. for 18 hours and the culture was centrifuged (12,000 rpm, 3 min) to collect cells. The cells were screened to give a transformant having a heat-resistant malate dehydrogenase activity.

That is, the collected cells were suspended in 1 ml of 0.1M potassium phosphate (pH 7.5) and the cells in the suspension were disrupted with glass beads. After disrupting, the resultant suspension was subjected to centrifugation (12,000 rpm, 5 min) to remove cell residue. The obtained crude enzyme solution was heated at 65° C. for 30 minutes and malate dehydrogenase activity was determined.

As a result of screening of about 10,000 colonies, one strain capable of producing heat-resistant MAD was found. The plasmid of the strain was found to contain an about 1.9 kbp insertional DNA and the plasmid was named pMDH1. The restriction enzyme map of the insertional DNA of pMDH1 is shown in FIG. 1.

EXAMPLE 4

Determination of Nucleotide Sequence

A subclone was prepared by cleaving about 1.9 kbp insertional DNA of pMDH1 with various restriction enzymes. The nucleotide sequence of the various subclones was identified by a conventional method with the use of Chemiluminescent DNA Sequencing Kit (manufactured by Toyo Boseki Kabushiki Kaisha, Japan). The identified nucleotide sequence and amino acid sequence are shown in Sequence Lists. The molecular weight determined based on the amino acid sequence was about 35,500 which was very close to the molecular weight (about 38,000) of malate dehydrogenase from *Bacillus stearothermophilus* ATCC 12016.

EXAMPLE 5

Preparation of *Eschelichia coli* Transformant

The competent cell of Eschelichia coli JM109 was transformed with pMDH1 to give a transformant JM109 (pMDH1).

EXAMPLE 6

Production of Heat-Resistant MAD

The above-mentioned LB medium (6 l) was dispensed to a 10 l-jar fermenter and autoclaved at 121° C. for 15 minutes. After cooling, 6 ml each of 50 mg/ml ampicillin (manufactured by Nakarai Tesque, Japan) and 200 mM IPTG (manufactured by Nihon Seika Corp., Japan), separately sterilized by filtration, was added thereto. A culture (60 ml) of *Eschelichia coli* JM109 (pMDH1) cultured in a medium having the same composition as above at 37° C. for 18 hours was inoculated to the above medium and the medium was cultured with aeration at 37° C. for 19 hours. The heat-resistant malate dehydrogenase activity after culture was 7.7 U/ml.

The culture (6 l) was subjected to centrifugation to collect cells and the cells were suspended in 280 ml of 50 mM potassium phosphate buffer (pH 7.5) and disrupted in a Dynomill (manufactured by WAB, Switzerland) by a conventional method. The resultant suspension was centrifuged at 8,000 rpm for 20 minutes to give a crude enzyme solution of heat-resistant MAD. The crude enzyme solution thus obtained was treated at 65° C. for 30 minutes to inactivate the malate dehydrogenase derived from the host and denucleated with polyethyleneimine. The heat-resistant MAD fraction was recovered by precipitation with ammonium sulfate and resuspended in the above-mentioned buffer (16 ml). The resuspension was heated at 60° C. for 16 hours. After the heat treatment, the resultant suspension was desalted with Sephadex G-25. The desalted enzyme solution was adjusted to pH 4.0 with acetic acid and subjected to CM Sepharose CL-6B (Pharmacia LKB, Sweden) chromatography to give a purified heat-resistant MAD product. The heat-resistant MAD product which underwent CM Sepharose CL-6B chromatography migrated as a single band on SDS-PAGE and the activity yield was 49%.

The purification from the transformant is summarized in Table 3. The physicochemical properties of the heat-resistant MAD obtained by the above method are shown in Table 4.

TABLE 3

Purification of heat-resistant MAD from *Escherichia coli* JM109 (pMDH1)

| step | total activity (U) | specific activity (U/mg-protein) | yield (%) |
|---|---|---|---|
| Dynomill disrupted solution | 46200 | — | 100 |
| heat-treated solution I | 37800 | 4.56 | 82 |
| polyethyleneimine-treated solution | 37400 | 6.46 | 81 |
| resuspension of ammonium sulfate precipitation | 37700 | 34.1 | 82 |
| heat-treated solution II | 32400 | 40.9 | 70 |
| G-25 desalted solution | 31800 | 83.0 | 69 |
| acid-treated solution | 31800 | 105.3 | 69 |
| CM Sepharose | 22800 | 203.0 | 49 |

TABLE 4

Physical and chemical properties of heat-resistant MAD from *Escherichia coli* JM109 (pMDH1)

| item | |
|---|---|
| Action | L-Malate + NAD$^+$ ⟷ Oxaloacetate + NADH + H$^+$ |
| Substrate specificity | specific oxidation of L-malic acid or specific reduction of oxaloacetic acid |
| Optimum temperature | 70° C. |
| Optimum pH | pH 8.0 |
| Heat stability | not more than 70° C. |
| pH stability | pH 3.0–9.0 |
| Isoelectric point | 4.8 |
| Molecular weight | 140,000 (gel filtration) 38,000 (SDS-PAGE) 35,500 (amino acid sequence) |
| Km value | 4.3 × 10$^{-6}$M (oxaloacetic acid) |
| Specific activity | 203 U/mg-protein |

A comparison of Table 1 and Table 3 readily indicates that the method for producing the heat-resistant MAD of the present invention enables production of the enzyme at higher purity in a larger amount as compared with the enzyme purified from wild type *Bacillus stearothermophilus* ATCC 12016.

In addition, a comparison of Table 2 and Table 4 reveals that the heat-resistant MAD produced by the transformant is superior to the heat-resistant MAD produced by *Bacillus stearothermophilus* ATCC 12016 in terms of heat stability.

EXAMPLE 7

Preparation of Reagent for GOT Determination, Comprising Use of Heat-Resistant MAD Derived From *Eschelichia coli* JM109 (pMDH1)

The following solution was prepared as a reagent for GOT determination.

| | |
|---|---|
| Lactate dehydrogenase | 500 U/l |
| Heat-resistant MAD | 1000 U/l |
| L-Aspartic acid | 200 mmol/l |
| α-Ketoglutaric acid | 10 mmol/l |
| NADH | 0.16 mmol/l |
| Tris-HCl buffer (pH 7.5) | 80 mmol/l |

The heat-resistant MAD was prepared from *Eschelichia coli* JM109 (pMDH1) by the method of Example 6.

The above-mentioned reagent was stored at 40° C. and residual malate dehydrogenase activity was measured at 1, 2, 4, 7, 10, 14, 21 and 32 days of storage. The results are shown in FIG. 2 with ○ and the activity was retained by 99% by 1-day storage, 97% by 2-day storage, 95% by 4-day storage, 94% by 7-day storage, 92% by 10-day storage, 91% by 14-day storage, 81% by 21-day storage and 74% by 32-day storage.

Figure 3:
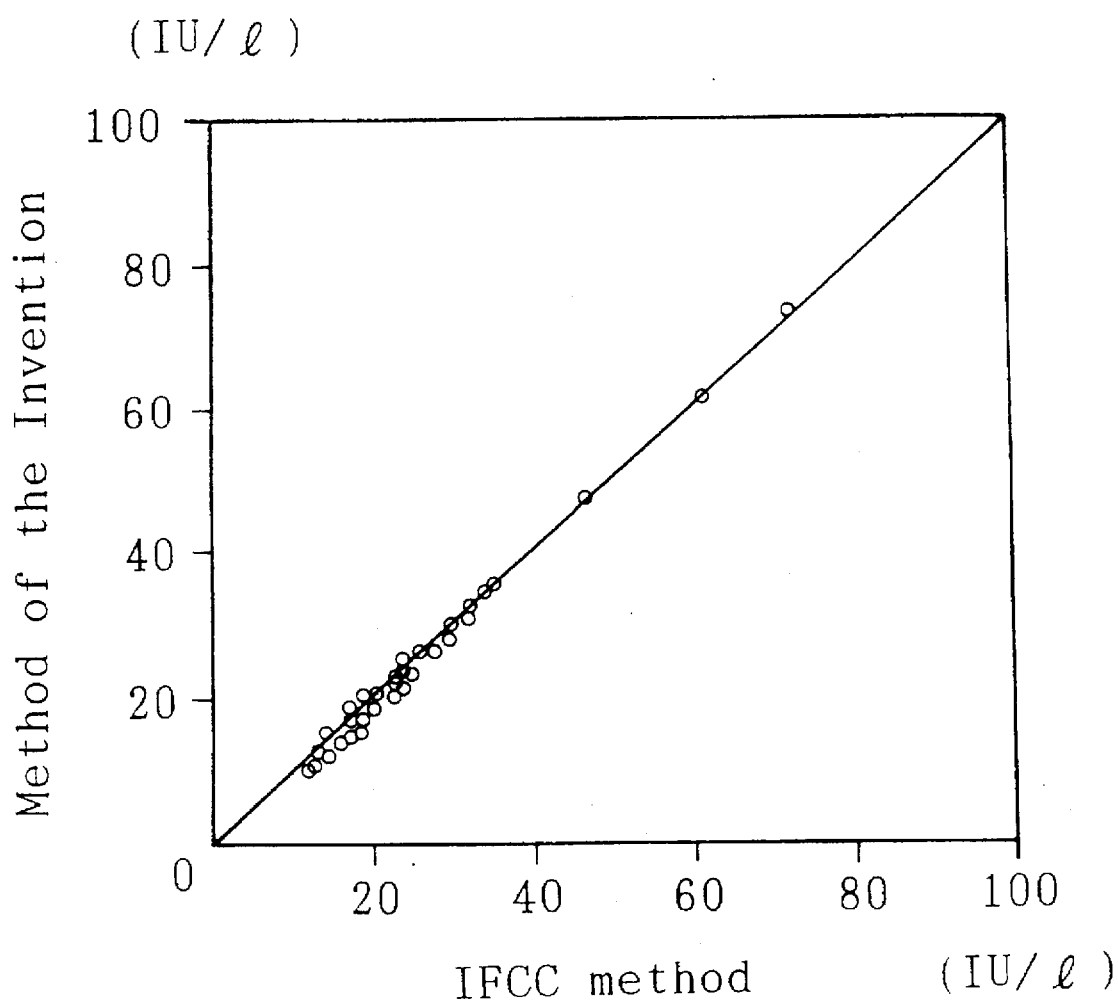
FIG. 3 shows a correlation between the determination of GOT activity in serum using the reagent of the present invention and the determination by IFCC method using the MAD of the present invention.

The correlation between the determination of GOT in serum using the above-mentioned reagent and the determination by IFCC (International Federation of Clinical Chemistry) method is shown in FIG. 3, which was found to be superior.

EXAMPLE 8

Preparation of Reagent for GOT Determination, Using Heat-Resistant MAD Derived From *Bacillus stearothemophitus* ATCC 12016

As the reagent for GOT determination, a solution of the composition of Example 7 was prepared. Note that an enzyme prepared by the method of Example 1 from *Bacillus stearothermophilus* ATCC 12016 was used as the heat-resistant MAD.

The above-mentioned reagent was stored at 40° C. and residual malate dehydrogenase activity was measured at 1, 2, 4, 7, 10, 14, 21 and 32 days of storage. The results are shown in FIG. 2 with ● and the activity was retained by 99% by 1-day storage, 97% by 2-day storage, 93% by 4-day storage, 90% by 7-day storage, 80% by 10-day storage, 72% by 14-day storage, 63% by 21-day storage and 45% by 32-day storage.

COMPARATIVE EXAMPLE 1

Preparation of Reagent for Determining GOT Activity, Using Malate Dehydrogenase Derived From Swine Heart As the reagent for GOT determination, a solution of the composition of Example 7 was prepared. Note that a commercially available enzyme derived from swine heart was used in place of the heat-resistant MAD.

The above-mentioned reagent was stored at 40° C. and residual malate dehydrogenase activity was measured at 1, 2, 4, 7, 10, 14, 21 and 32 days of storage. The results are shown in FIG. 2 with ▲ and the activity was retained by 17% by 1-day storage, 2% by 2-day storage, 1% by 4-day storage, 1% by 7-day storage, 0% by 10-day storage, 0% by 14-day storage, 0% by 21-day storage and 0% by 32-day storage.

COMPARATIVE EXAMPLE 2

Preparation of Reagent For GOT Determination, Using Malate Dehydrogenase Derived From the Strain of the Genus Thermus As the reagent for GOT determination, a solution of the composition of Example 7 was prepared. Note that a commercially available enzyme derived from the strain of the genus Thermus was used in place of the heat-resistant MAD.

The above-mentioned reagent was stored at 40° C. and residual malate dehydrogenase activity was measured at 1, 2, 4, 7, 10, 14, 21 and 32 days of storage. The results are shown in FIG. 2 with □ and the activity was retained by 99% by 1-day storage, 97% by 2-day storage, 92% by 4-day storage, 87% by 7-day storage, 75% by 10-day storage, 66% by 14-day storage, 45% by 21-day storage and 31% by 32-day storage.

The results indicate the superior stability of the heat-resistant MAD produced by the transformant, into which a gene derived from a bacterium belonging to the genus Bacillus has been incorporated, while being contained in the reagent for GOT determination.

---

What is claimed is:

1. A purified heat-resistant malate dehydrogenase, which shows a residual activity of at least 60% after preserving at 40° C. for 10 days in a solution state and which further has the following properties:

Action: reversibly catalyzing the following reaction:

L-maleic acid+NAD⁺—oxaloacetic acid+NADH+H⁺

Substrate specificity: specific oxidation of L-maleic acid or specific reduction of oxaloacetic acid pH stability: pH 3.0–9.0

Molecular weight: 140,000 (gel filtration), 38,000 (SDS-PAGE)

Amino acid sequence: SEQ ID NO: 2.

2. The purified heat-resistant malate dehydrogenase of claim 1, which is obtained from *Bacillus stearothermophilus* ATCC 12016.

3. The purified heat-resistant malate dehydrogenase of claim 1, which is produced by a prokaryotic transformant carrying a gene having the nucleotide sequence depicted in SEQ ID NO: 1.

4. The purified heat-resistant malate dehydrogenase of claim 1, which is further characterized by having the following properties:

Optimum temperature: 70° C.

Optimum pH: 8.0

Isoelectric point: 4.8

Km value: $4.3 \times 10^{-6}$

5. The purified heat-resistant malate dehydrogenase of claim 4, which is obtained from *Bacillus stearothermophilus* ATCC 12016.

6. The purified heat-resistant malate dehydrogenase of claim 4, which is produced by a prokaryotic transformant carrying a gene having the nucleotide sequence depicted in SEQ ID NO: 1.

* * * * *

UNITED STATES PATENT AND TRADEMARK OFFICE
CERTIFICATE OF CORRECTION

PATENT NO. : 5,744,342
DATED : April 28, 1998
INVENTOR(S) : SOGABE et al.

It is certified that error appears in the above-identified patent and that said Letters Patent is hereby corrected as shown below:

In Column 2, line 53: *"stearothermophiLus"* should read --*stearothermophilus*--.
In Column 4, line 45: "Bacilus" should read --*Bacillus* --.
In Column 6, line 31: *"subtitis"* should read --*subtilis*--.
In Column 9, line 7: *"mophitus"* should read --*mophilus* --.
In Column 14, line 5: "(pMDHI)" should read --(pMDH1)--.
In Column 15, line 17: *"stearothemophitus"* should read --*stearothermophilus*--.
In Column 16, line 24: "Thermus" should read --*Thermus*--.
In Column 16, line 38: "Bacillus" should read --*Bacillus*--.

Signed and Sealed this

Tenth Day of November 1998

Attest:

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1912 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus stearothermophilus
        ( B ) STRAIN: ATCC12016

( x i ) SEQUENCE DESCRIPTION: SEQ ID NO:1:

```
AATCAACTAC  GCGATTGAAC  ACGGCCGCAA  GTCGGTGACG  CTCGTTCATA  AAGGAAACAT        60
```

-continued

| | | | | | |
|---|---|---|---|---|---|
| TATGAAATTC | ACCGAAGGCG | CGTTTAAAAA | CTGGGGTTAT | GAATTGGCGG | AGGAAGAATT | 120 |
| CGCCGACAAA | GTGTTCACGT | GGGCGCAATA | CGACCGAATC | GTTGAAACGG | AAGGCAAGGA | 180 |
| AGCGGCGAAC | AAAGCGCTTG | CTGATGCGGA | ACGGTCCGGC | AAAATCATTA | TCAAAGATGT | 240 |
| CATCGCCGAC | ATCTTCCTGC | AACAAATTTT | GACGCGTCGC | GCGAATTTGA | CGTCATCGCG | 300 |
| ACGATGAACT | TAAACGCCGA | CTACATTTCC | GACGCGCTGG | CCGCTCAAGT | CGGCGGCATC | 360 |
| GGCATCGCGG | CGGGGGCCAA | CATCAACTAC | GAAACCGGCC | ACGCGATTTT | CGAAGCGACG | 420 |
| CACGGCACGG | CTGCCGAATA | CGCAGGCTTG | ACAAAGTCAC | CGTCGTCCGT | CATTCTCTCG | 480 |
| GCGTCATGAT | GTTTGAGCAT | CTTGGTTGGA | ACGAAGCAGC | GAAATTGATC | ATCAAAGCGA | 540 |
| TGGAGAAAAC | CATCGCCGCG | AAAATCGTCA | CGTATGACTT | CGCCCGCCTG | ATGGAAGGGG | 600 |
| CGACGGAAGT | GAAATGCTCC | GAATTTGCTG | ATGCGCTCAT | CCGCAATATG | GACTAACCTT | 660 |
| TGAAGGAAAG | GGATGGCAAA | CG ATG GCG ATG AAA CGG AAA AAA ATC TCG GTG | | | | 712 |
| | | Met Ala Met Lys Arg Lys Lys Ile Ser Val | | | |
| | | 1 5 10 | | | |

| ATC | GGC | GCC | GGA | TTC | ACG | GGG | GCG | ACG | ACG | GCG | TTC | CTT | TTG | GCG | CAA | 760 |
|---|---|---|---|---|---|---|---|---|---|---|---|---|---|---|---|---|
| Ile | Gly | Ala | Gly | Phe | Thr | Gly | Ala | Thr | Thr | Ala | Phe | Leu | Leu | Ala | Gln | |
| | | | | 15 | | | | 20 | | | | | | 25 | | |

| AAA | GAG | CTC | GGC | GAC | GTC | GTG | TTG | GTC | GAT | ATT | CCG | CAG | CTT | GAG | AAC | 808 |
|---|---|---|---|---|---|---|---|---|---|---|---|---|---|---|---|---|
| Lys | Glu | Leu | Gly | Asp | Val | Val | Leu | Val | Asp | Ile | Pro | Gln | Leu | Glu | Asn | |
| | | | 30 | | | | | 35 | | | | | 40 | | | |

| CCA | ACG | AAA | GGG | AAG | GCG | CTC | GAT | ATG | CTC | GAG | GCA | AGC | CCG | GTG | CTC | 856 |
|---|---|---|---|---|---|---|---|---|---|---|---|---|---|---|---|---|
| Pro | Thr | Lys | Gly | Lys | Ala | Leu | Asp | Met | Leu | Glu | Ala | Ser | Pro | Val | Leu | |
| | | 45 | | | | | 50 | | | | | 55 | | | | |

| GGC | TTT | GAC | GCG | AAT | ATC | ATC | GGC | ACA | TCG | GAT | TAC | GCT | GAC | ACA | GCC | 904 |
|---|---|---|---|---|---|---|---|---|---|---|---|---|---|---|---|---|
| Gly | Phe | Asp | Ala | Asn | Ile | Ile | Gly | Thr | Ser | Asp | Tyr | Ala | Asp | Thr | Ala | |
| | 60 | | | | | 65 | | | | | 70 | | | | | |

| GAT | TCC | GAC | ATC | GTC | GTC | ATC | ACA | GCA | GGC | ATC | GCC | CGC | AAG | CCG | GGC | 952 |
|---|---|---|---|---|---|---|---|---|---|---|---|---|---|---|---|---|
| Asp | Ser | Asp | Ile | Val | Val | Ile | Thr | Ala | Gly | Ile | Ala | Arg | Lys | Pro | Gly | |
| 75 | | | | | 80 | | | | | 85 | | | | | 90 | |

| ATG | AGC | CGC | GAC | GAT | TTG | GTG | ACG | ACG | AAC | CAA | AAA | ATT | ATG | AAG | CAA | 1000 |
|---|---|---|---|---|---|---|---|---|---|---|---|---|---|---|---|---|
| Met | Ser | Arg | Asp | Asp | Leu | Val | Thr | Thr | Asn | Gln | Lys | Ile | Met | Lys | Gln | |
| | | | | 95 | | | | | 100 | | | | | 105 | | |

| GTG | ACG | AAG | GAA | GTC | GTC | AAA | TAC | TCG | CCG | AAC | TGC | TAC | ATC | ATC | GTC | 1048 |
|---|---|---|---|---|---|---|---|---|---|---|---|---|---|---|---|---|
| Val | Thr | Lys | Glu | Val | Val | Lys | Tyr | Ser | Pro | Asn | Cys | Tyr | Ile | Ile | Val | |
| | | | 110 | | | | | 115 | | | | | 120 | | | |

| TTG | ACG | AAC | CCG | GTC | GAT | GCG | ATG | ACG | TAT | ACG | GTC | TTT | AAG | GAA | TCC | 1096 |
|---|---|---|---|---|---|---|---|---|---|---|---|---|---|---|---|---|
| Leu | Thr | Asn | Pro | Val | Asp | Ala | Met | Thr | Tyr | Thr | Val | Phe | Lys | Glu | Ser | |
| | | 125 | | | | | 130 | | | | | 135 | | | | |

| GGA | TTC | CCG | AAA | AAC | CGC | GTC | ATC | GGC | CAG | TCG | GGC | GTC | TTG | GAT | ACG | 1144 |
|---|---|---|---|---|---|---|---|---|---|---|---|---|---|---|---|---|
| Gly | Phe | Pro | Lys | Asn | Arg | Val | Ile | Gly | Gln | Ser | Gly | Val | Leu | Asp | Thr | |
| | 140 | | | | | 145 | | | | | 150 | | | | | |

| GCG | CGC | TTC | CGC | ACG | TTC | GTC | GCC | GAG | GAG | CTG | AAC | ATT | TCG | GTA | AAA | 1192 |
|---|---|---|---|---|---|---|---|---|---|---|---|---|---|---|---|---|
| Ala | Arg | Phe | Arg | Thr | Phe | Val | Ala | Glu | Glu | Leu | Asn | Ile | Ser | Val | Lys | |
| 155 | | | | | 160 | | | | | 165 | | | | | 170 | |

| GAT | GTC | ACT | GGG | TTT | GTT | TTA | GGC | GGC | CAT | GGC | GAT | GAC | ATG | GTG | CCG | 1240 |
|---|---|---|---|---|---|---|---|---|---|---|---|---|---|---|---|---|
| Asp | Val | Thr | Gly | Phe | Val | Leu | Gly | Gly | His | Gly | Asp | Asp | Met | Val | Pro | |
| | | | | 175 | | | | | 180 | | | | | 185 | | |

| CTC | GTC | CGC | TAC | TCG | TAC | GCC | GGC | GGC | ATT | CCG | CTC | GAA | AAA | CTC | ATT | 1288 |
|---|---|---|---|---|---|---|---|---|---|---|---|---|---|---|---|---|
| Leu | Val | Arg | Tyr | Ser | Tyr | Ala | Gly | Gly | Ile | Pro | Leu | Glu | Lys | Leu | Ile | |
| | | | 190 | | | | | 195 | | | | | 200 | | | |

| CCG | AAA | GAT | CGT | TTG | GAC | GCC | ATC | GTT | GAG | CGG | ACG | CGC | AAA | GGC | GGC | 1336 |
|---|---|---|---|---|---|---|---|---|---|---|---|---|---|---|---|---|
| Pro | Lys | Asp | Arg | Leu | Asp | Ala | Ile | Val | Glu | Arg | Thr | Arg | Lys | Gly | Gly | |
| | | 205 | | | | | 210 | | | | | 215 | | | | |

| GGT | GAA | ATC | GTC | AAC | CTG | CTC | GGC | AAC | GGC | AGC | GCC | TAC | TAC | GCA | CCG | 1384 |
|---|---|---|---|---|---|---|---|---|---|---|---|---|---|---|---|---|
| Gly | Glu | Ile | Val | Asn | Leu | Leu | Gly | Asn | Gly | Ser | Ala | Tyr | Tyr | Ala | Pro | |
| | | 220 | | | | | 225 | | | | | 230 | | | | |

-continued

```
GCC GCC TCG CTT GTC GAA ATG GTC GAA GCG ATT TTG AAA GAC CAG CGC        1432
Ala Ala Ser Leu Val Glu Met Val Glu Ala Ile Leu Lys Asp Gln Arg
235             240             245             250

CGC ATT TTG CCG GCG ATC GCC TAC CTT GAA GGC GAA TAC GGC TAT GAA        1480
Arg Ile Leu Pro Ala Ile Ala Tyr Leu Glu Gly Glu Tyr Gly Tyr Glu
                255             260             265

GGC ATT TAT TTG GGC GTG CCG ACG ATC CTC GGC GGC AAC GGC ATC GAG        1528
Gly Ile Tyr Leu Gly Val Pro Thr Ile Leu Gly Gly Asn Gly Ile Glu
        270             275             280

AAA GTG ATC GAG CTC GAG CTG ACC GAA GAG GAA AAA GCG CGC TCG CCA        1576
Lys Val Ile Glu Leu Glu Leu Thr Glu Glu Glu Lys Ala Arg Ser Pro
        285             290             295

AAT CCG TCG AAT CCG TTA AAA ATG TCA TGC GCA TCG TGG AAT AGC GGC        1624
Asn Pro Ser Asn Pro Leu Lys Met Ser Cys Ala Cys Trp Asn Ser Gly
300             305             310

GAG GCA AAA ATT CCG GCA TTG CCC GGA TTT TTG TCC CAC AGT CAA            1669
Glu Ala Lys Ile Arg Ala Leu Pro Gly Phe Leu Ser His Ser Gln
315             320             325

TGAAAGCGCT TTCTAGACAA CGAAGGGGTG GGAACATGTT GAAAAAACGA AAGCTCGGGA       1729

GACCGATCGG GGAAATTCAA GCGGGGGAAA AGCTCGTGTT CCAAGCCGCC ATCGAAGACA       1789

AAGACTTGCT TCTTTATCTT GGGCTGACGG ATGATGCCAA TCCGCTCTAT ATCCAGCATG       1849

ATTATGCTTC ACAGACGCCG TTTGGAAAAC CGGTCGTGCC GCCGGTCATG TTGACGGGGA       1909

TGA                                                                    1912
```

( 2 ) INFORMATION FOR SEQ ID NO:2:

( i ) SEQUENCE CHARACTERISTICS:
        ( A ) LENGTH: 329 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Met Lys Arg Lys Lys Ile Ser Val Ile Gly Ala Gly Phe Thr
 1               5                  10                  15

Gly Ala Thr Thr Ala Phe Leu Leu Ala Gln Lys Glu Leu Gly Asp Val
                20                  25                  30

Val Leu Val Asp Ile Pro Gln Leu Glu Asn Pro Thr Lys Gly Lys Ala
            35                  40                  45

Leu Asp Met Leu Glu Ala Ser Pro Val Leu Gly Phe Asp Ala Asn Ile
        50                  55                  60

Ile Gly Thr Ser Asp Tyr Ala Asp Thr Ala Asp Ser Asp Ile Val Val
65                  70                  75                  80

Ile Thr Ala Gly Ile Ala Arg Lys Pro Gly Met Ser Arg Asp Asp Leu
                85                  90                  95

Val Thr Thr Asn Gln Lys Ile Met Lys Gln Val Thr Lys Glu Val Val
                100                 105                 110

Lys Tyr Ser Pro Asn Cys Tyr Ile Ile Val Leu Thr Asn Pro Val Asp
            115                 120                 125

Ala Met Thr Tyr Thr Val Phe Lys Glu Ser Gly Phe Pro Lys Asn Arg
        130                 135                 140

Val Ile Gly Gln Ser Gly Val Leu Asp Thr Ala Arg Phe Arg Thr Phe
145                 150                 155                 160

Val Ala Glu Glu Leu Asn Ile Ser Val Lys Asp Val Thr Gly Phe Val
                165                 170                 175

Leu Gly Gly His Gly Asp Asp Met Val Pro Leu Val Arg Tyr Ser Tyr
```

|  | 180 |  |  |  |  |  | 185 |  |  |  |  | 190 |  |  |
|---|---|---|---|---|---|---|---|---|---|---|---|---|---|---|
| Ala | Gly | Gly 195 | Ile | Pro | Leu | Glu | Lys 200 | Leu | Ile | Pro | Lys | Asp 205 | Arg | Leu | Asp |
| Ala | Ile 210 | Val | Glu | Arg | Thr | Arg 215 | Lys | Gly | Gly | Gly | Glu 220 | Ile | Val | Asn | Leu |
| Leu 225 | Gly | Asn | Gly | Ser | Ala 230 | Tyr | Tyr | Ala | Pro | Ala 235 | Ala | Ser | Leu | Val | Glu 240 |
| Met | Val | Glu | Ala | Ile 245 | Leu | Lys | Asp | Gln | Arg 250 | Arg | Ile | Leu | Pro | Ala 255 | Ile |
| Ala | Tyr | Leu | Glu 260 | Gly | Glu | Tyr | Gly | Tyr 265 | Glu | Gly | Ile | Tyr | Leu 270 | Gly | Val |
| Pro | Thr | Ile 275 | Leu | Gly | Gly | Asn | Gly 280 | Ile | Glu | Lys | Val | Ile 285 | Glu | Leu | Glu |
| Leu | Thr 290 | Glu | Glu | Glu | Lys | Ala 295 | Arg | Ser | Pro | Asn | Pro 300 | Ser | Asn | Pro | Leu |
| Lys 305 | Met | Ser | Cys | Ala | Cys 310 | Trp | Asn | Ser | Gly | Glu 315 | Ala | Lys | Ile | Arg | Ala 320 |
| Leu | Pro | Gly | Phe | Leu 325 | Ser | His | Ser | Gln |  |  |  |  |  |  |  |